United States Patent
Ding et al.

(10) Patent No.: US 10,624,928 B2
(45) Date of Patent: Apr. 21, 2020

(54) COMPOSITION FOR TREATMENT OF JOINT DISEASE AND METHOD THEREOF

(71) Applicant: Buddhist Tzu Chi Medical Foundation, Hualien, Hualien County (TW)

(72) Inventors: Dah-Ching Ding, Hualien (TW); Kun-Chi Wu, Hualien (TW)

(73) Assignee: Hualien Tzu Chi Hospital, Buddhist Tzu Chi Medical Foundation, Hualien (TW)

( * ) Notice: Subject to any disclaimer, the term of this patent is extended or adjusted under 35 U.S.C. 154(b) by 279 days.

(21) Appl. No.: 14/708,399

(22) Filed: May 11, 2015

(65) Prior Publication Data
US 2016/0095886 A1    Apr. 7, 2016

(30) Foreign Application Priority Data
Oct. 6, 2014    (TW) .............................. 103134710 A

(51) Int. Cl.
*A61K 35/28*    (2015.01)
*A61K 31/728*    (2006.01)
(Continued)

(52) U.S. Cl.
CPC ............ *A61K 35/28* (2013.01); *A61K 9/0019* (2013.01); *A61K 31/728* (2013.01); *C12N 5/0607* (2013.01); *C12N 5/0667* (2013.01)

(58) Field of Classification Search
None
See application file for complete search history.

(56) References Cited

U.S. PATENT DOCUMENTS

2009/0196901 A1*  8/2009  Guilak ................... A61L 27/54
                                                              424/423
2012/0114609 A1*  5/2012  Callegaro ............. A61K 35/16
                                                              424/93.3

FOREIGN PATENT DOCUMENTS

JP    2004-507454 A    3/2004
JP    2009-523438 A    6/2009
(Continued)

OTHER PUBLICATIONS

Hass ("Different populations and sources of human mesenchymal stem cells (MSC): A comparison of adult and neonatal tissue derived MSC" Cell Communication and Signaling, 2011, 9:12, 1-14).*
(Continued)

*Primary Examiner* — Robert J Yamasaki
*Assistant Examiner* — Charles Zoltan Constantine
(74) *Attorney, Agent, or Firm* — McCarter & English, LLP; Yu Lu

(57) ABSTRACT

The present invention provides a pharmaceutical composition comprising mesenchymal stem cells, a hyaluronan and a pharmaceutically acceptable carrier. The pharmaceutical composition is used for the treatment of the joint disease. The mesenchymal stem cells in the composition are at least one selected from the group consisting of infra-patellar fat pad stromal cells, bone marrow stem cells, Wharton's jelly stem cells and adipose derived stem cells. The concentration of the hyaluronan is in a range from 25% (v/v) to 75% (v/v). The present invention further provides a method for treating a joint disease, comprising a step of administrating a composition containing mesenchymal stem cells, a hyaluronan and a pharmaceutically acceptable carrier to an injured joint tissue of a subject.

10 Claims, 14 Drawing Sheets
Specification includes a Sequence Listing.

(51) Int. Cl.
  *C12N 5/077*  (2010.01)
  *C12N 5/0775*  (2010.01)
  *A61K 9/00*  (2006.01)
  *C12N 5/074*  (2010.01)

(56) References Cited

FOREIGN PATENT DOCUMENTS

| | | | |
|---|---|---|---|
| JP | 2010-532370 A | 10/2010 | |
| JP | 2015-502905 A | 1/2015 | |
| WO | WO 0180865 A3 * | 4/2002 | ........... C12N 5/0663 |
| WO | 2005/094888 A1 | 10/2005 | |
| WO | 2006/134921 A1 | 12/2006 | |

OTHER PUBLICATIONS

Bonab ("Aging of mesenchymal stem cells in vitro" BMC Cell Biology, 7:14, 2006, 1-7).*
Buckley ("Functional properties of cartilaginous tissues engineered from infrapatellar fat pad-derived mesenchymal stem cells" Journal of Biomechanics, 43 (2010) 920-926).*
Fraser ("Hyaluronan: its nature, distribution, functions and turnover" Journal of Internal Medicine, 1997, 242 27-33).*
Ding, Wu, Chou, Hung, Liu, and Chu, "Human Infrapatellar Fat Pad-Derived Stromal Cells Have More Potent Differentiation Capacity Than Other Mesenchymal Cells and Can Be Enhanced by Hyaluronan" Cell Transplantation, vol. 24, 1221-1232, 2015, EPublication date May 21, 2014 (Year: 2014).*
Bannuru, "Theraputic trajectory following intra-articular hyaluronic acid injection in knee osteoarthritis—meta-analysis", Osteoarthritis and Cartilage, Osteoarthritis Research Society International, 19 (2011), 611-619. (Year: 2011).*
Huri "Infrapatellar Fat Pad-Derived Stem Cell-Based Regenerative Strategies in Orthopedic Surgery" Knee Surgery and Related Research, 2018 30(3), 179-186. (Year: 2018).*
Sharma Mesenchymal stem or stromal cells: a review of clinical applications and manufacturing practices, Transfusion, 2014, 54(5), 1418-1437. (Year: 2014).*
Chung et al., Influence of three-dimensional hyaluronic acid microenvironments on mesenchymal stem cell chondrogenesis. Tissue Eng Part A. Feb. 2009;15(2):243-54.
Koh et al., Mesenchymal stem cell injections improve symptoms of knee osteoarthritis. Arthroscopy. Apr. 2013;29(4):748-55.
Lin, Development of injectable hyaluronan modified thermo-responsive hydrogel for adipose-derived stem cell based articular cartilage tissue engineering, Kaohsiung Medical University thesis, Dec. 5, 2012, 6 pages, abstract only.
Nakata et al., Mechanical Stimulation and Hyaluronic Acid for Chondrogenic Differentiation of Three-dimensional Tissue Using Human Synovium-derived Stem Cell. Clinical Orthopaedics Surgery, Osaka University Graduate School of Medicine. 2007;42(4):313-318.
Suhaeb et al., Hyaluronic acid with or without bone marrow derived-mesenchymal stem cells improves osteoarthritic knee changes in rat model: a preliminary report. Indian J Exp Biol. Jun. 2012;50(6):383-90.
Abstract of WO2005094888.
Abstract of JP2004507454 (A).
Abstract of JP2009523438 (A).
Abstract of JP2010532370 (A).
Abstract of JP2015502905 (A).
Abstract of WO2006134921.

* cited by examiner

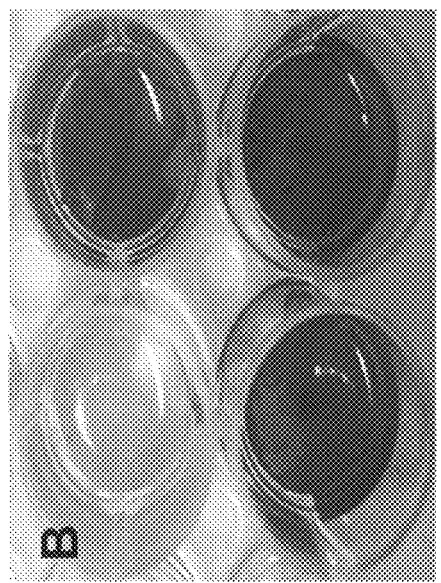
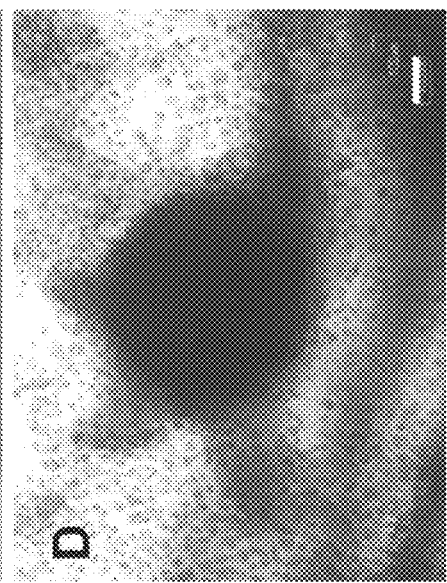
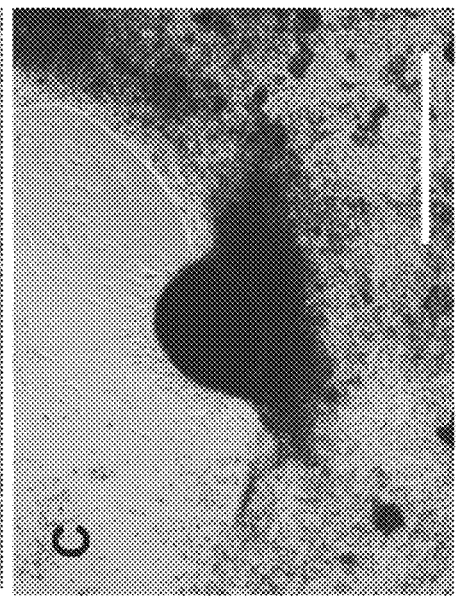
FIG. 4A  FIG. 4B  FIG. 4C  FIG. 4D

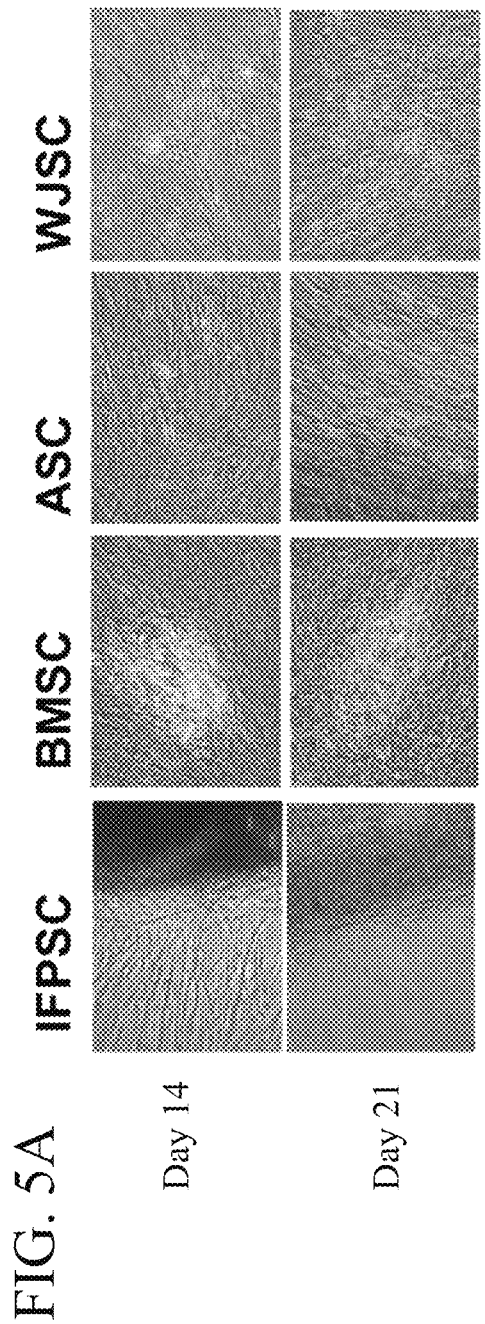
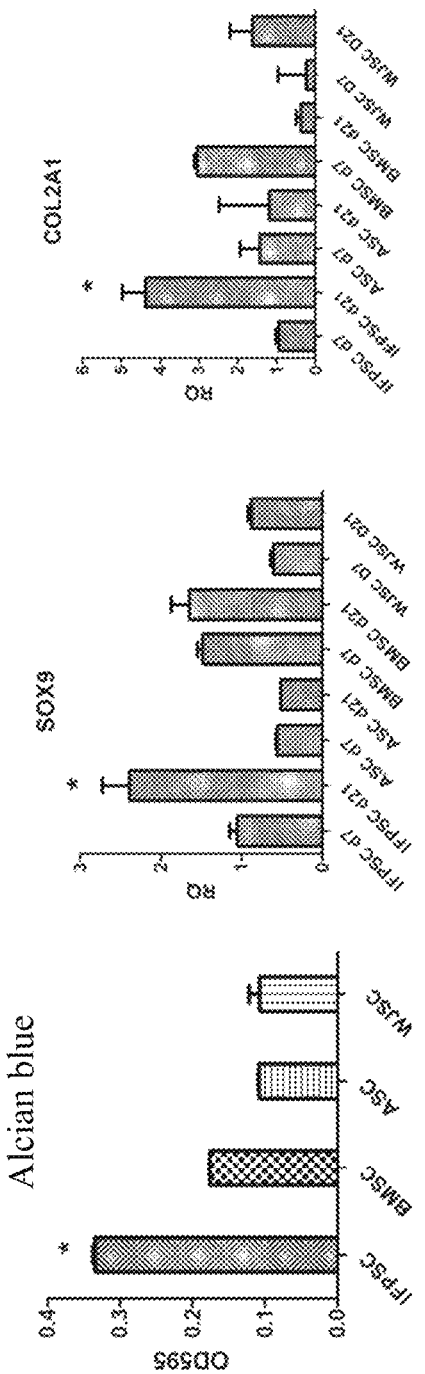
FIG. 5A
FIG. 5B
FIG. 5C
FIG. 5D

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: SOX9 Forward Sequence
<220> FEATURE:
<221> NAME/KEY: primer_bind
<222> LOCATION: (1)..(18)

<400> SEQUENCE: 1
cttccgcgac gtggacat                                              18

<210> SEQ ID NO 2
<211> LENGTH: 18
<212> TYPE: DNA
<213> ORGANISM: Artificial Sequence

```
<220> FEATURE:
<223> OTHER INFORMATION: SOX9 Reverse Sequence
<220> FEATURE:
<221> NAME/KEY: primer_bind
<222> LOCATION: (1)..(18)

<400> SEQUENCE: 2
gttgggcggc aggtactg                                              18

<210> SEQ ID NO 3
<211> LENGTH: 21
<212> TYPE: DNA
<213> ORGANISM: Artificial Sequence
<220> FEATURE:
<223> OTHER INFORMATION: COL2A1 Forward Sequence
<220> FEATURE:
<221> NAME/KEY: primer_bind
<222> LOCATION: (1)..(21)

<400> SEQUENCE: 3
caacactgcc aacgtccaga t                                          21

<210> SEQ ID NO 4
<211> LENGTH: 24
<212> TYPE: DNA
<213> ORGANISM: Artificial Sequence
<220> FEATURE:
<223> OTHER INFORMATION: COL2A1 Reverse Sequence
<220> FEATURE:
<221> NAME/KEY: primer_bind
<222> LOCATION: (1)..(24)

<400> SEQUENCE: 4
tcttgcagtg gtaggtgatg ttct                                       24

<210> SEQ ID NO 5
<211> LENGTH: 23
<212> TYPE: DNA
<213> ORGANISM: Artificial Sequence
<220> FEATURE:
<223> OTHER INFORMATION: GAPDH Forward Sequence
<220> FEATURE:
<221> NAME/KEY: primer_bind
<222> LOCATION: (1)..(23)

<400> SEQUENCE: 5
tctcctctga cttcaacagc gac                                        23

<210> SEQ ID NO 6
<211> LENGTH: 22
<212> TYPE: DNA
<213> ORGANISM: Artificial Sequence
<220> FEATURE:
<223> OTHER INFORMATION: GAPDH Reverse Sequence
<220> FEATURE:
<221> NAME/KEY: primer_bind
<222> LOCATION: (1)..(22)

<400> SEQUENCE: 6
ccctgttgct gtagccaaat tc                                         22
```

COMPOSITION FOR TREATMENT OF JOINT DISEASE AND METHOD THEREOF

CROSS-REFERENCE TO RELATED APPLICATION

This application claims foreign priority under 35 U.S.C. § 119(a) to patent application Ser. No. 10/313,4710, filed on Oct. 6, 2014, in the Intellectual Property Office of Ministry of Economic Affairs, Republic of China (Taiwan, R.O.C.), the entire content of which patent application is incorporated herein by reference.

REFERENCE TO SEQUENCE LISTINGS

This application contains a Sequence Listing which has been submitted electronically via EFS-web in ASCII format, and is hereby incorporated by reference in its entirety. Said ASCII copy, created on Feb. 12, 2020, is named Seq_Listing_123710_04501.txt, and is 1,772 bytes in size.

BACKGROUND OF THE INVENTION

1. Field of the Invention

The present invention relates to a pharmaceutical composition, and more particularly to a composition comprising mesenchymal stem cells, a hyaluronan and a pharmaceutically acceptable carrier.

2. Description of Related Art

Osteoarthritis (hereinafter also referred to as OA) is a worldwide health problem among the elderly, affecting over 70% of Americans between the ages of 55 and 70 years old. It is caused by progressive chondral damage due to chronic trauma or diseases. Articular cartilage has a limited capacity for repair because of the avascularity and low cellular mitotic activity.

The cause of osteoarthritis formulation involves several pathological mechanisms, including enzymatic degradation of the extracellular matrix (hereinafter also referred to as ECM), deficient new matrix formation, cell death, and abnormal activation and hypertrophic differentiation of cartilage cells. Many treatment methods have been developed to decrease pain and improve the affected functions in individuals. However, current strategies such as total joint arthroplasty are unable to restore the native structure of cartilage and may even increase further risk of articulation damage.

Recent researches have developed a treatment for osteoarthritis by bone and cartilage generated from the bone marrow mesenchymal stem cells (hereinafter also referred to as BMSCs). While this technique is appealing, the harvest of bone marrow is painful and yields a limited number of stem cells, especially in the elderly. Thus, an extensive expansion of the stem cells in culture is desired. Adipose-derived mesenchymal stem cells (hereinafter also referred to as ASCs) are currently the best choice since they can be obtained in larger amounts with less morbidity and can be easily expanded in vitro. In addition to regeneration activity, ASCs also exhibit immunosuppressive properties. Recently, cells with stem cell characteristics have been reported in the infra-patellar fat pad (hereinafter also referred to as IFP).

The ECM provides a micro-environment for cells to maintain homeostasis and differentiate to the specific tissues. In the ECM, hyaluronan (hereinafter also referred to as HA) is the main glycosaminoglycan in the mesenchyme of early chondrogenesis and is native in the cartilage tissue. As the major physiological component of the articular cartilage matrix, HA is particularly abundant in synovial fluid. This polymer plays a role in cartilage homeostasis and is involved in cellular processes such as cell morphogenesis, proliferation, and wound repair. It is also widely used for the intra-articular treatment of OA. However, the effect of HA micro-environment on mesenchymal stem cells (hereinafter also referred to as MSCs) differentiation has rarely been reported.

SUMMARY OF THE INVENTION

The present invention provides a pharmaceutical composition comprising mesenchymal stem cells, a hyaluronan and a pharmaceutically acceptable carrier.

In one embodiment of the present invention, the composition is used for treating a joint disease, wherein the joint disease is articular cartilage defect, chronic articular rheumatism, arthritis deformans or periarthritis humeroscapularis.

In one embodiment of the present invention, the mesenchymal stem cells are cultured to passage 3 to passage 6. In another embodiment of the present invention, the composition comprises $1.6 \times 10^7$ to $1 \times 10^9$ cells of the mesenchymal stem cells. The mesenchymal stem cells are at least one selected from the group consisting of infra-patellar fat pad stromal cells, bone marrow stem cells, Wharton's jelly stem cells and adipose derived stem cells. Preferably, the mesenchymal stem cells are infra-patellar fat pad stromal cells.

In one embodiment of the present invention, the mesenchymal stem cells are induced to produce glycosaminoglycans.

In one embodiment of the present invention, the concentration of the hyaluronan is in a range from 25% (v/v) to 75% (v/v). Preferably, the concentration of the hyaluronan is in a range from 25% (v/v) to 50% (v/v). Most preferably, the concentration of the hyaluronan is 25% (v/v).

The present invention further provides a method for treating a joint disease comprising a step of administrating an effective amount of a composition comprising mesenchymal stem cells, a hyaluronan and a pharmaceutically acceptable carrier to an injured joint tissue of a subject.

In one embodiment of the present invention, the pharmaceutical composition of the present invention is administrated to an injured joint tissue of a subject by injection administration, wherein the joint disease is articular cartilage defect, chronic articular rheumatism, arthritis deformans or periarthritis humeroscapularis.

In one embodiment of the present invention, the mesenchymal stem cells are cultured to passage 3 to passage 6 and the number of the mesenchymal stem cells is between $1.6 \times 10^7$ and $1 \times 10^9$ cells.

In one embodiment of the prevent invention, the mesenchymal stem cells are at least one selected from the group consisting of infra-patellar fat pad stromal cells, bone marrow stem cells, Wharton's jelly stem cells and adipose derived stem cells. Preferably, the mesenchymal stem cells are infra-patellar fat pad stromal cells.

BRIEF DESCRIPTION OF THE DRAWINGS

FIGS. 4A-4D show multipotent differentiation capability of the IFPSCs by adipogenesis by oil red staining (FIG. 4A); osteogenesis by Alizarin Red staining (FIG. 4B); and chondrogenesis by Alcian blue staining (FIGS. 4C and 4D). Scale bar: 100 μm in FIGS. 4A and 4B, 1000 μm in FIGS. 4C and 4D.

FIGS. 5A-5D show that the IFPSCs are more chondrogenic than other mesenchymal stem cells. The capability for chondrogenesis of various mesenchymal stem cells is shown by Alcian blue staining (FIG. 5A) and the staining level (FIG. 5B), which is measured at OD595, at day 14 and day 21. Expressions of SOX 9 (FIG. 5C) and COL2A1 (FIG. 5D) at different induction days are measured by qRT-PCR, $*p<0.05$.

FIG. 7A shows gross pictures of the IFPSCs after 5 days of culture with 25% (v/v), 50% (v/v), 75% (v/v), and 100% (v/v) of HA. FIG. 7B shows proliferations of the IFPSCs are not affected by HA at different concentrations. Scale bar: 1000 μm.

DETAILED DESCRIPTION OF THE PREFERRED EMBODIMENTS

Figure 1A:
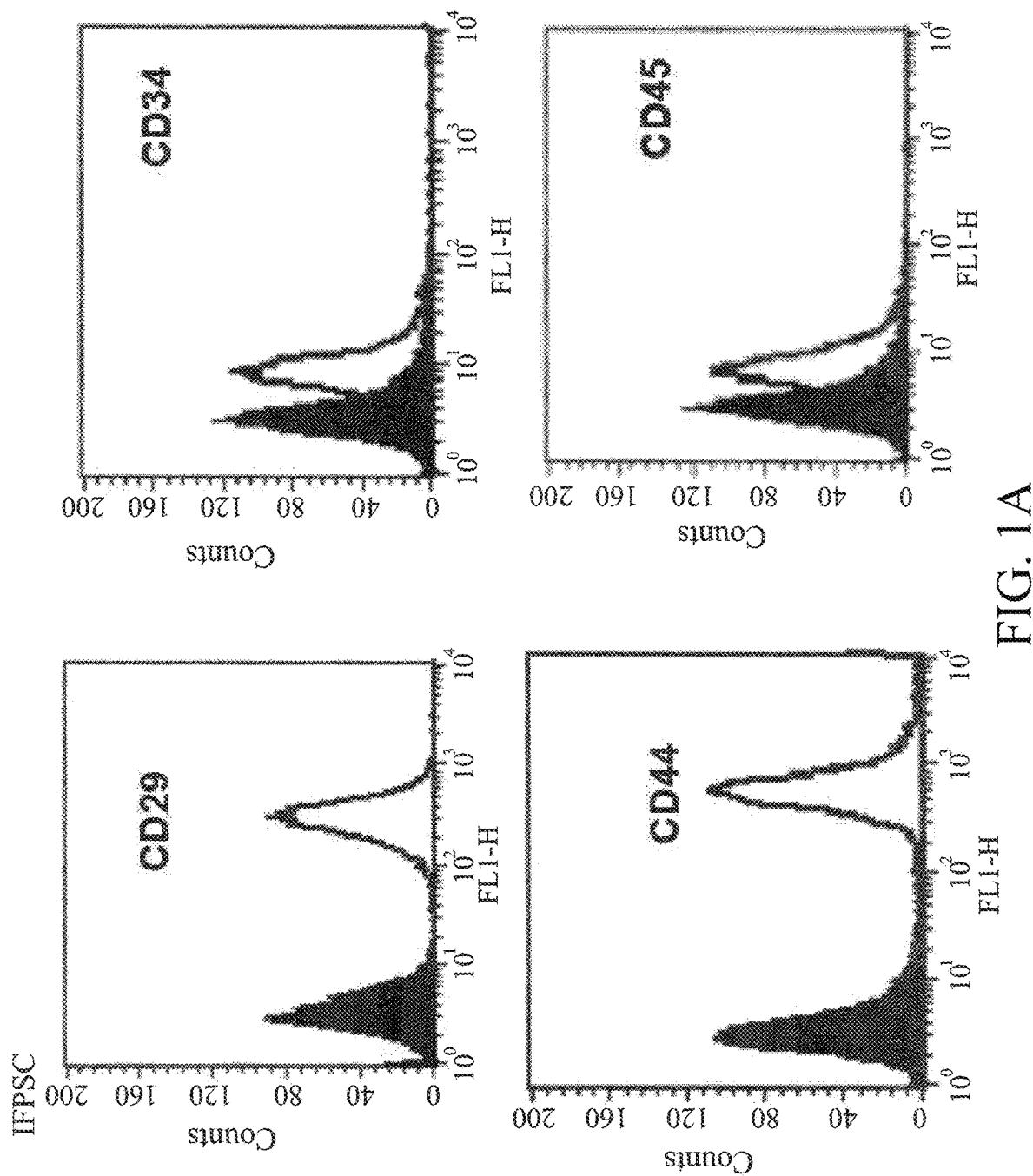
FIGS. 1A-1D show the cell markers of infra-patellar fat pad stromal cells (hereinafter also referred to as IFPSCs) (FIG. 1A), bone marrow mesenchymal stem cells (BMSCs) (FIG. 1B), Wharton's jelly stem cells (hereinafter also referred to as WJSCs) (FIG. 1C), and adipose stem cells (ASCs) (FIG. 1D).
Figure 1A:
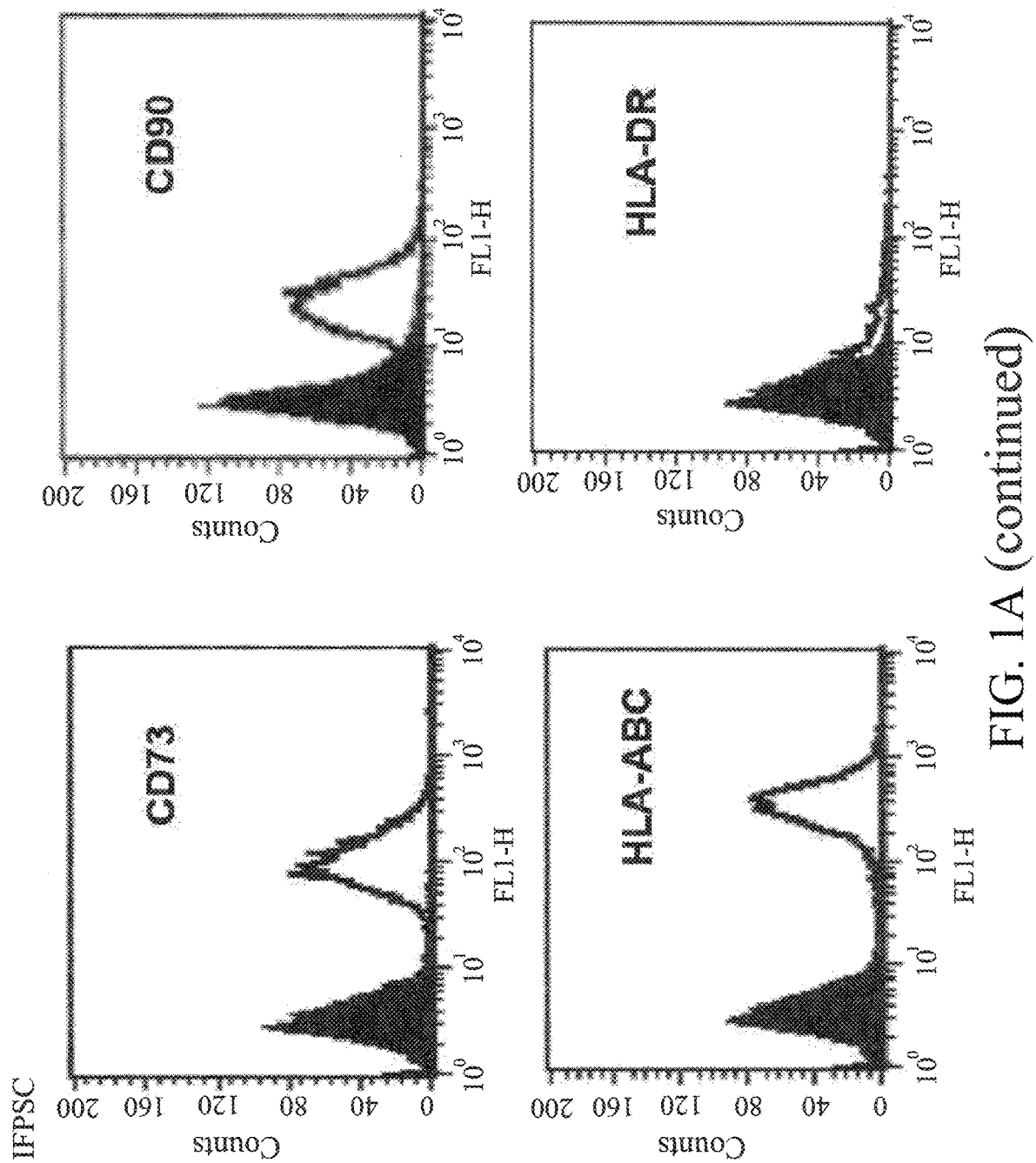
Figure 1B:
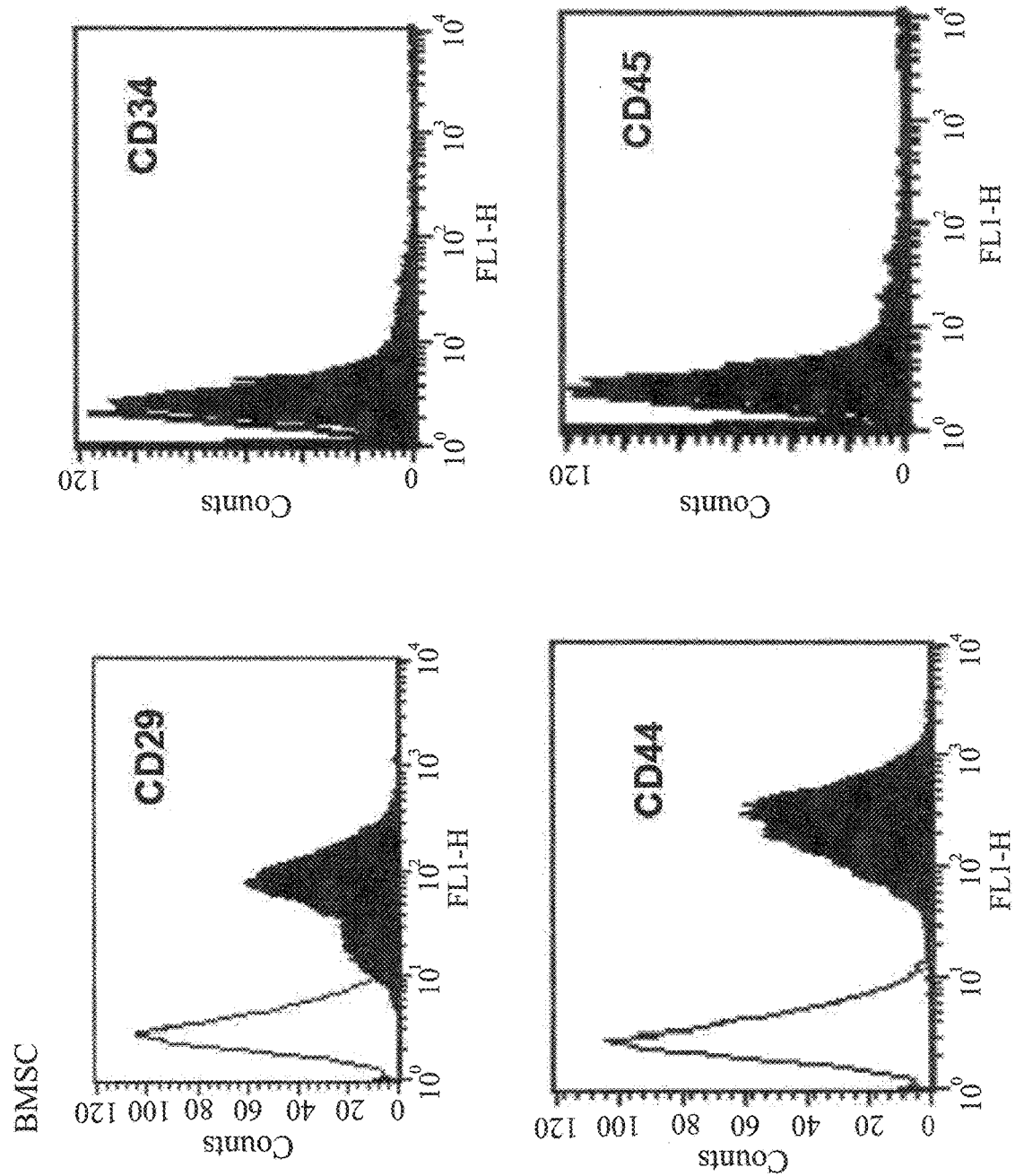
Figure 1B:
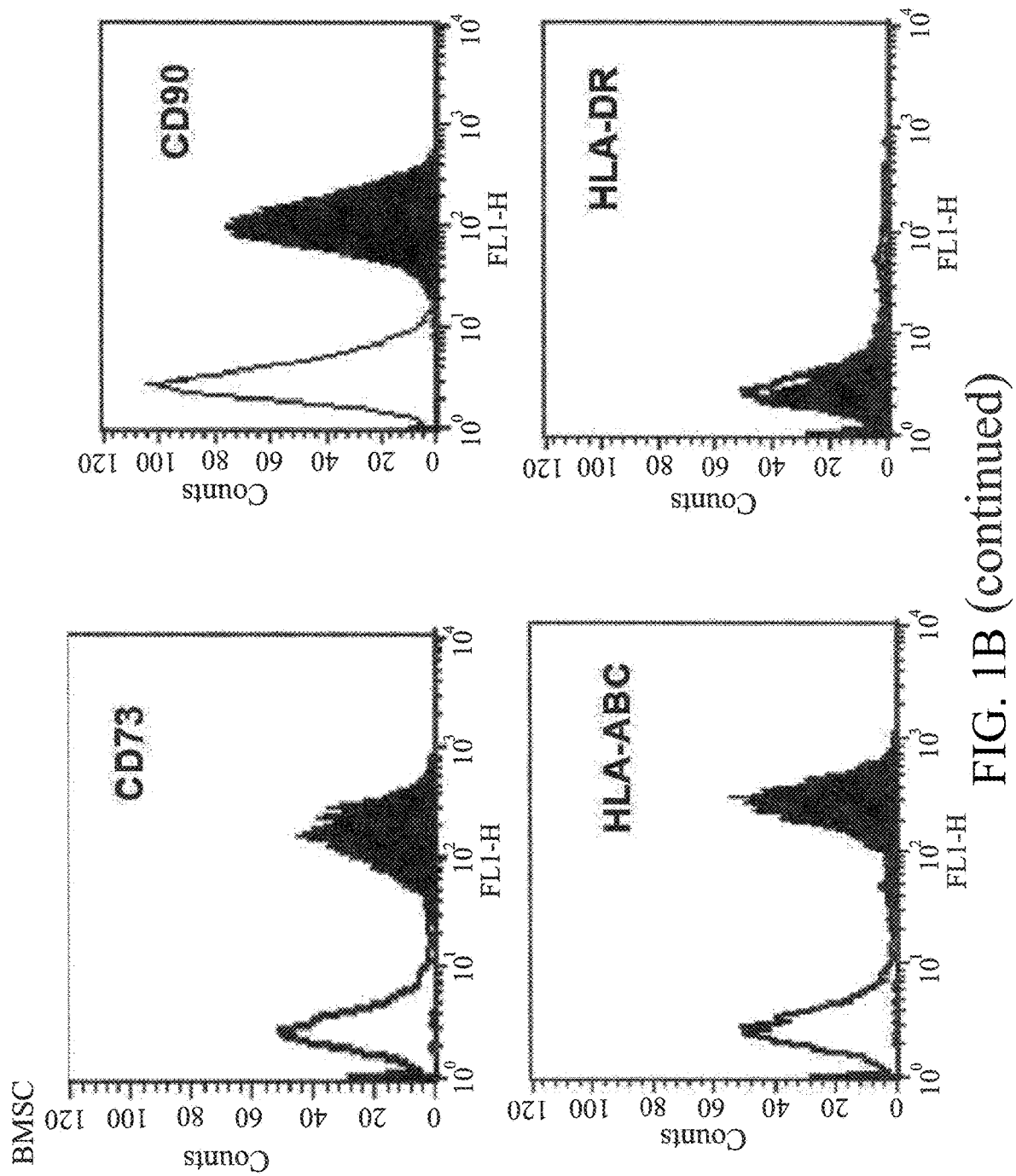
Figure 1C:
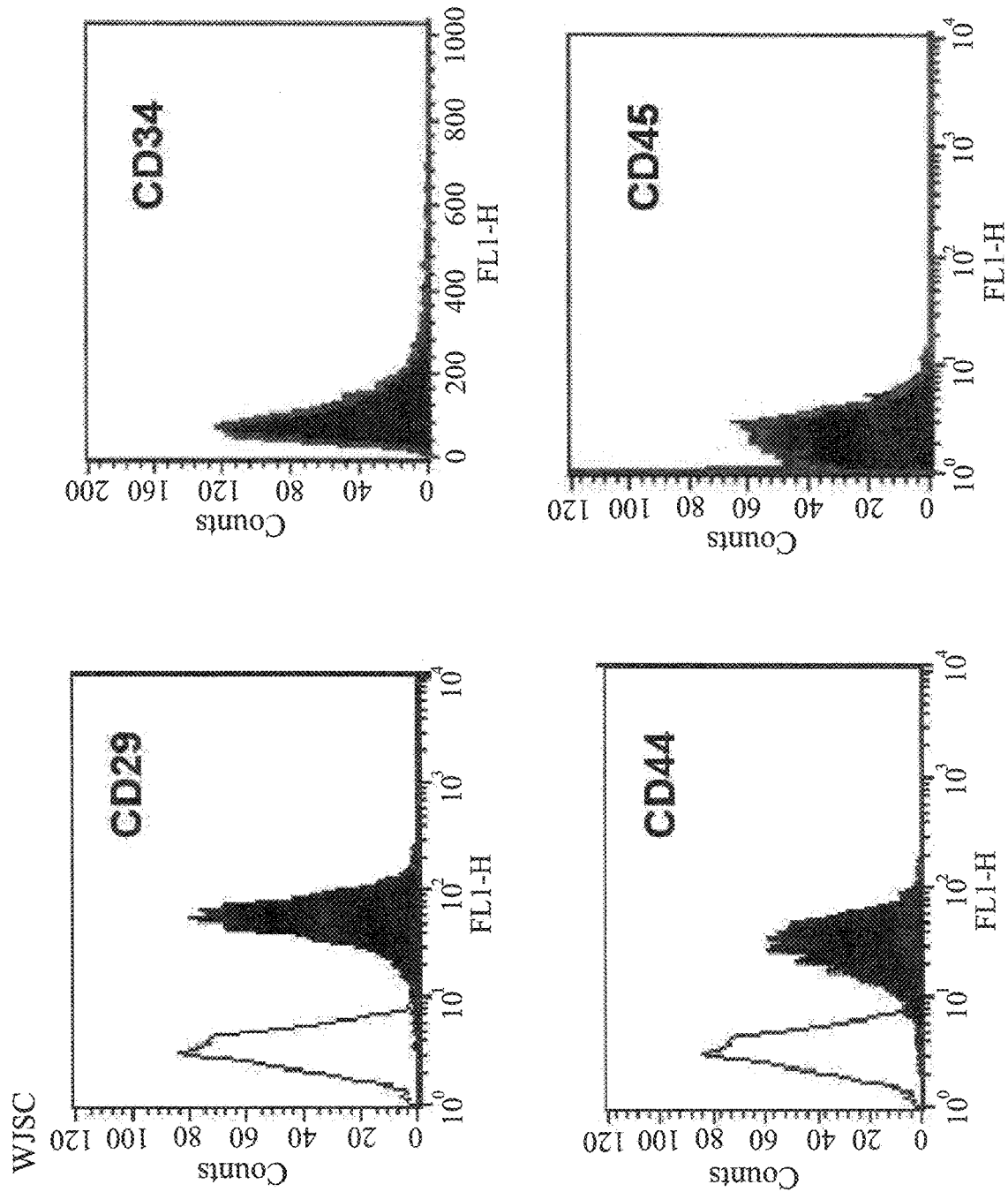
Figure 1C:
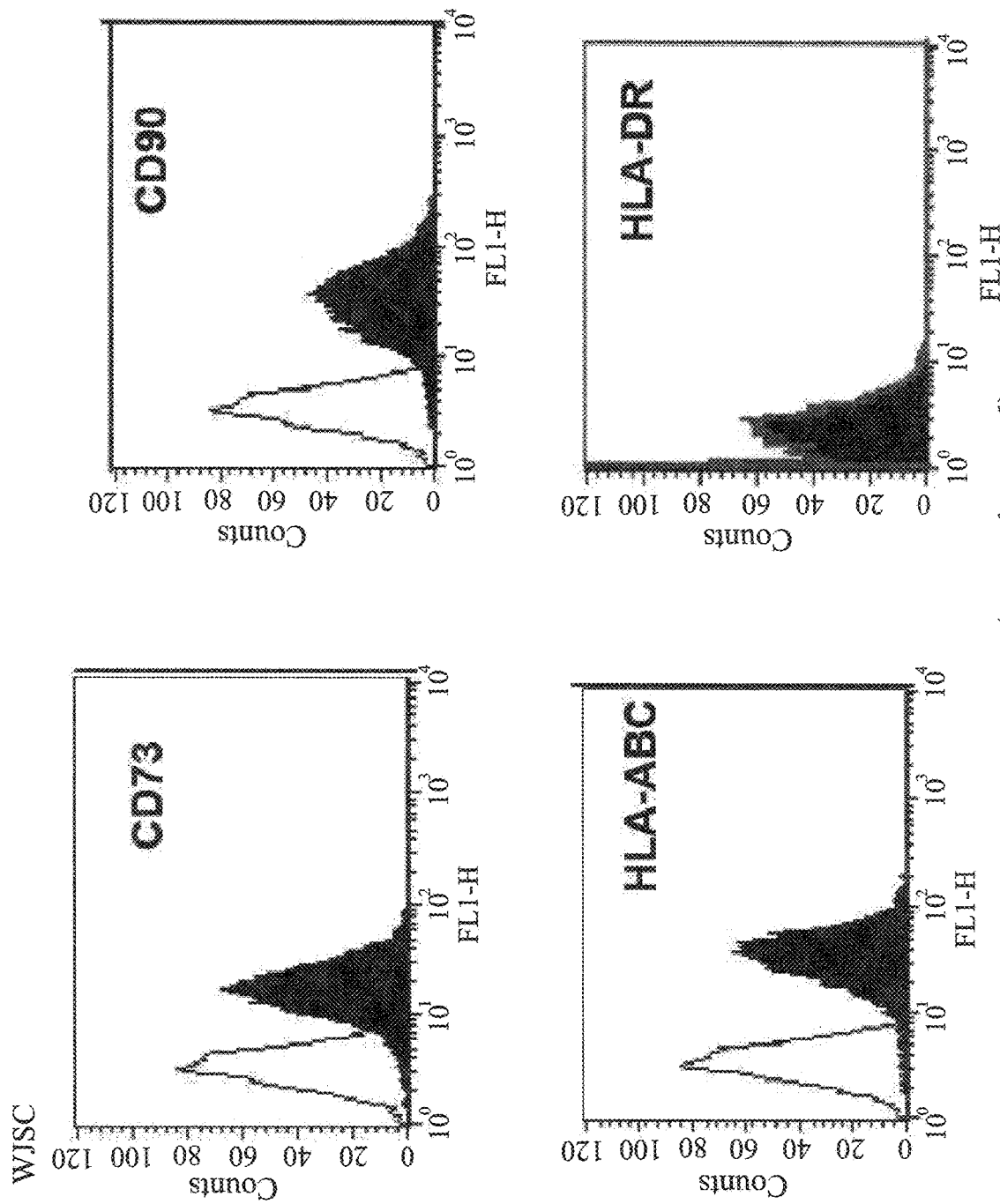
Figure 1D:
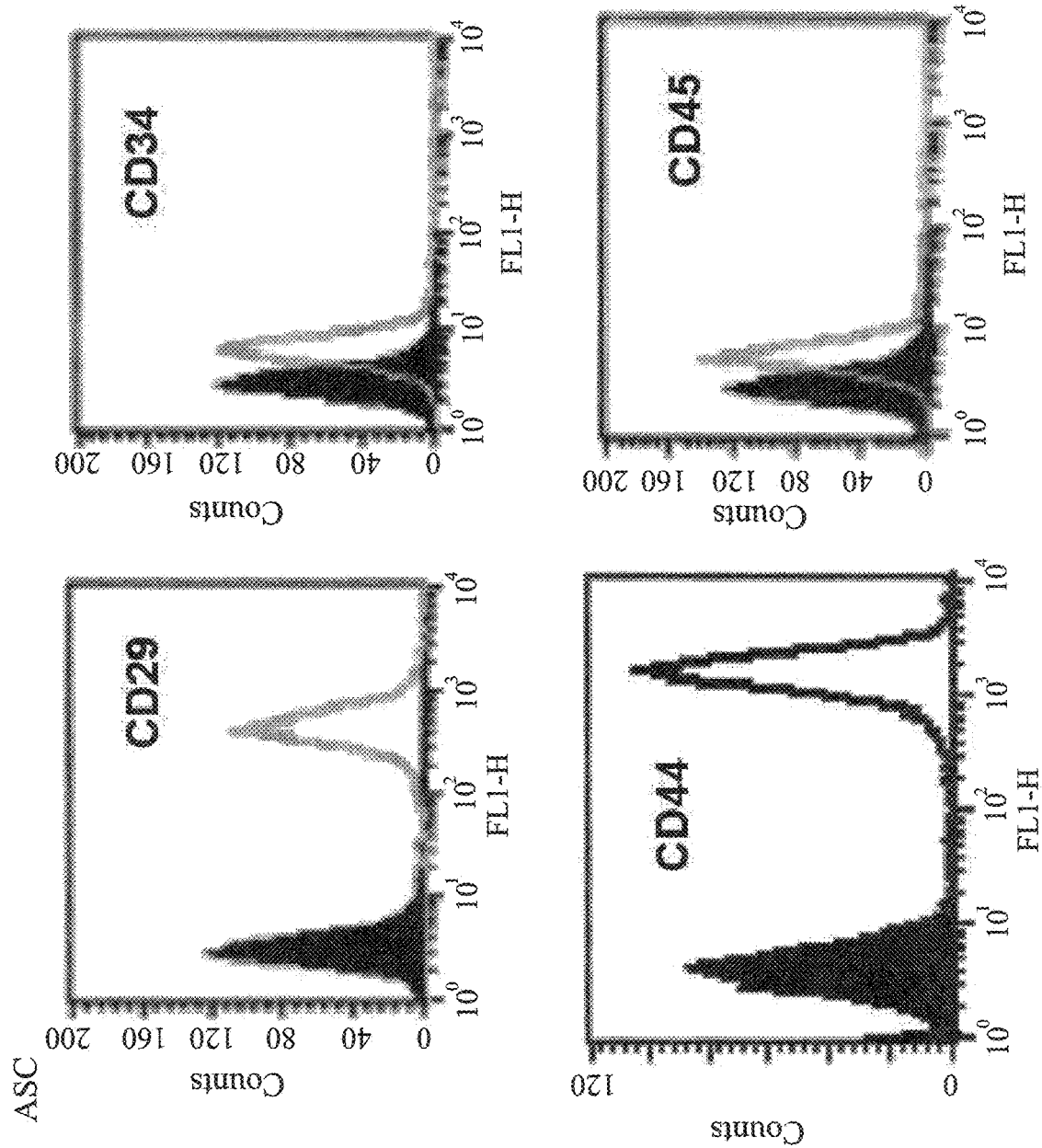
Figure 1D:
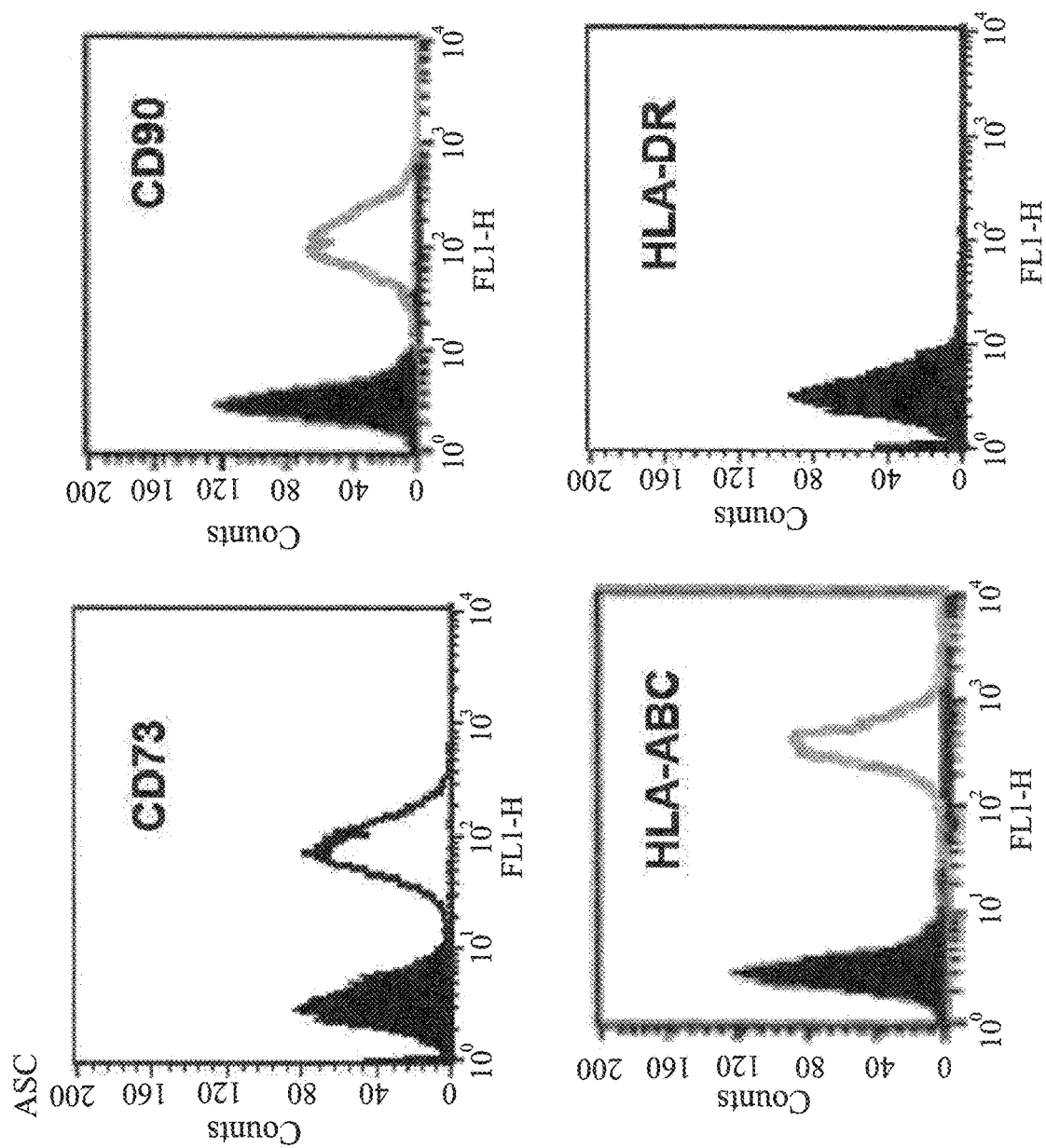

The following specific examples are used for illustrating the present invention. A person skilled in the art can easily conceive the other advantages and effects of the present invention. The present invention can also be implemented by different specific cases be enacted or application, the details of the instructions can also be based on different perspectives and applications in various modifications and changes do not depart from the spirit of the present invention.

Unless the context indicates otherwise, the singular forms "a" and "an" and "the" used in the specification and the appended claims include the plural forms.

Unless the context indicates otherwise, the term "or" used in the specification and the appended claims means both "and" as well as "or".

The present invention provides a pharmaceutical composition comprising mesenchymal stem cells, a hyaluronan and a pharmaceutically acceptable carrier. According to one embodiment of the present invention, the composition is used for treating a joint disease, wherein the joint disease is articular cartilage defect, chronic articular rheumatism, arthritis deformans or periarthritis humeroscapularis. The present invention provides treating a joint disease, more specifically, repairing the articular cartilage and facilitating the recovery of various cartilages.

According to one embodiment of the present invention, the articular cartilage contains has a chondrocytes density in a range from 6,800 to 24,000 cells/mm³. Thus, for regenerating cartilage in this density, it is estimated that $1.6\times10^7$ cells may be required to repair 600 mm³ of cartilage area. Therefore, according to one embodiment of the present invention, the preparation of IFPSCs for repairing the cartilage tissue includes excising the infra-patellar fat pad and manually processing and isolating IFPSCs, and it takes approximately one hour. Subsequently, the IFPSCs are cultured for 4-5 days to grow to sub-confluence, and then cultured for 10 days (at passage 3) to expand to $1.6\times10^7$ cells. It is estimated that the preparation can be accomplished within two weeks. According to one embodiment of the present invention, preferably, when the mesenchymal stem cells are cultured to passage 3 to passage 6, the number of the mesenchymal stem cells is between $1.6\times10^7$ and $1\times10^9$ cells. Most preferably, when the mesenchymal stem cells are cultured to passage 5, the number of the mesenchymal stem cells is $1\times10^8$ cells.

According to one embodiment of the present invention, the mesenchymal stem cells are at least one selected from the group consisting of infra-patellar fat pad stromal cells (IFPSCs), bone marrow stem cells (BMSCs), Wharton's jelly stem cell (WJSCs) and adipose derived stem cells (ASCs). Preferably, the mesenchymal stem cells are infra-patellar fat pad stromal cells.

According to one embodiment of the present invention, both of the cell surface marker profile and the growth kinetics of the IFPSCs are in concordance with those of ASCs from abdominal subcutaneous fat tissue. The CD34 and CD45 levels in the IFPSCs (9.0% and 11.0%) are higher than those in the BMSCs (0.3% and 0.5% respectively). Although the IFPSCs share most of the surface markers as the ASCs, the CD45 level in the IFPSCs is much higher (0.4%).

According to one embodiment of the present invention, in the presence of the chondrogenic medium, the mesenchymal stem cells (including IFPSCs, ASCs, BMSCs and WJSCs) are induced to produce glycosaminoglycans, which are major components of the ECM of cartilage tissue, and can be stained by Alcian Blue. Compared to other mesenchymal cells (including ASCs, BMSCs and WJSCs), the IFPSCSs show more significant Alcian Blue staining for chondrogenic inductions as well as higher expression levels of chondrogenic genes such as SOX9 and COL2A1.

According to one embodiment of the present invention, the present invention also shows that the mesenchymal stem cells have the chemotactic activity towards chondrocytes, indicating the potential directions of the mesenchymal stem cells toward the injured cartilage. The chemotactic activity seems to have no tissue specificity, since the mesenchymal stem cells from non-articular origin also have great chemotactic activity.

According to one embodiment of the present invention, the donor's age does not affect the proliferation rate, doubling time, telomere length, or osteogenic and chondrogenic differentiation capacities of the mesenchymal stem cells. When the mesenchymal stem cells are cultured to passage 3 to passage 6, they have stability and the cell properties comparable to progenitor cells. The cellular senescence often occurs after passage 10.

According to one embodiment of the present invention, various concentrations of hyaluronan (HA) have no promoting effect on the mesenchymal stem cells proliferation. However, HA may promote chondrogenesis of the mesenchymal stem cells. As HA being a native component in the cartilage tissue, it is used for the induction of chondrocytes from their progenitors in the joint. Further, HA is essential for cell-to-cell cross bridging for cell aggregation. In addition, HA is also the major component of synovial fluid which surrounds the IFP. Therefore, HA in the synovial fluid may contribute to a microenvironment that can induce chondrogenic differentiation of the mesenchymal stem cells during the injured tissues repair. In the present invention, the concentration of the HA is represented by volume percentage concentration. The concentrations of the HA used in the present invention is in a range from 0% (v/v) to 100% (v/v), preferably from 25% (v/v) to 75% (v/v). The concentration of 25% (v/v) of HA has the best effect on the chondrogenic differentiation. These results indicate that HA provides a suitable microenvironment for chondrocyte growth, and also enhances the chondrogenic differentiation of the mesenchymal stem cells.

According to one embodiment of the present invention, the present invention demonstrates that a combined injection of the mesenchymal stem cells (including ASCs, BMSCs and WJSCs) and HA in the injured joint tissues has better effect on chondrogenesis.

According to one embodiment of the present invention, in the composition comprising mesenchymal stem cells, a hyaluronan and a pharmaceutically acceptable carrier, for example, as the composition is used in a solid form, the pharmaceutically acceptable carrier can include binders, lubricants, disintegrating agents, excipients, hydrotropic agents, dispersants, stabilizers, suspending agents, colorants and flavors. As the composition is used in a liquid form, the pharmaceutically acceptable carrier can include buffering agents, preserving agents, analgetics, hydrotropic agents, isotonic agents and stabilizers.

In one embodiment of the present invention, HA also enhances the chondrogenic differentiation of the ASCs. In the concentration of 25% (v/v) of the HA, the chondrogenesis effect of the IFPSCSs is greater than that of the ASCs.

EXAMPLES

Procurement of Infra-Patellar Fat Pad (IFP) and Articular Cartilage Tissue

Primary human articular cartilage fragments were isolated from adult male through arthroscopy. After obtaining the approval from the Research Ethics Committee of the Buddhist Tzu Chi General Hospital and obtaining the informed consent from the participants, IFPs were harvested during total knee joint arthroplasty surgeries. Meanwhile, the stem cells (such as BMSCs, ASCs and WJSCs) from other sources were also harvested. The volume of IFPs was around 2×2×2 $cm^3$. The patients (n=2, both females) were aged more than 60 years (65 and 68 years).

Statistical Analysis

Herein, the results were expressed as mean±SD. Student's t-test was used to evaluate mean differences between the control and experimental groups. A value of $p<0.05$ was considered to be statistically significant. The proliferation rate of the IFPSCs was compared to the other three cell lines by using Mann-Whitney U test of multiple comparison.

Example 1 Derivation of Stromal Cells from Human IFPs

The harvested IFPs underwent a series of washes with phosphate-buffered saline (PBS, Biowest, Nuaille, France) and were digested with 0.1 mg/ml collagenase Ia (Sigma, St Louis, Mo., USA) at 37° C. for 60 minutes. After enzyme digestion, the resulting cells were collected and cultured in keratinocyte serum-free medium (KSFM, Gibco, Grand island, NY, USA) containing 5% fetal bovine serum (FBS) (Biological Industry, Kibbutz, Israel), n-acetyl cysteine (NAC) (Sigma-Aldrich, St Louis, Mo., USA), and L-ascorbic acid 2-phosphate (Sigma-Aldrich, St Louis, Mo., USA). The supernatant and debris in the culture dish were removed on the second day of culture, and the resulting IFPSCs cultures were denoted as passage 0. To prevent the spontaneous differentiation, the cultures were maintained at sub-confluent levels (less than 80% of confluence). The passage of the cultures was performed by using 2.5% trypsin/0.23 mM EDTA (Gibco, Grand island, NY, USA). XTT cell proliferation assays (Roche, Mannheim, Germany) were conducted in 96-well plate at a cell density of around 2000 cells/$cm^2$ on days 0, 3, and 7.

Example 2 Culture of Bone Marrow Mesenchymal Stem Cells (BMSCs), Adipose-Derived Mesenchymal Stem Cells (ASCs) and Wharton's Jelly Stem Cells (WJSCs)

BMSCs (n=1) were provided by the bone marrow bank of the Buddhist Tzu Chi General hospital. The BMSCs were cultured with α-MEM (Gibco, Grand island, NY, USA) supplemented with 10% FBS (Biological Industry, Kibbutz, Israel).

ASCs were derived from the subcutaneous tissue of the patient who underwent gynecologic surgery (n=1, female, 60 years of age). The human adipose tissue was cut into small pieces (1 to 2 $mm^3$), digested with 0.1 mg collagenase Ia (Sigma, St. Louis, Mo., USA), and incubated for 60 minutes at 37° C. The resulting cells were collected and cultured in KSFM (added with epidermal growth factor and bovine pituitary extract, Gibco, 17005-042, Grand island, NY, USA) with 5% FBS, NAC, and L-ascorbic acid-2-phosphate. The supernatant and debris were removed from the culture dish on day 2 of culture. To prevent spontaneous differentiation, the cultures were maintained at sub-confluent levels (less than 80% of confluence).

The collected human umbilical cord tissues (n=1) were mechanically cut by scissors along the midline, and then the vessels of the umbilical arteries, veins and outlining membranes were dissociated from the Wharton's jelly. The jelly was then cut into pieces smaller than 0.5 $cm^3$, treated with collagenase type 1 (Sigma, St Louis, Mo., USA) and incubated for 14 to 18 hours at 37° C. in a 95% air/5% $CO_2$ humidified atmosphere. The explants were then cultured in DMEM (Gibco, Grand island, NY, USA) containing 10% FBS and antibiotics at 37° C. in a 95% air/5% $CO_2$ humidified atmosphere. The explants were then left undisturbedly for 5 to 7 days, and then WJSCs were migrated from the explants.

Example 3 Analysis for the Surface Molecules of the Stem Cells by Flow Cytometry The surface molecules of the IFPSCs and BMSCs cultured to passage 3 or passage 4 were characterized by flow cytometry. The cells were detached with 2 mM EDTA in PBS, washed with PBS containing 2% bovine serum albumin and 0.1% sodium azide (Sigma, St. Louis, Mo., USA), and incubated with the antibodies conjugated with fluorescein isothiocyanate or phycoerythrin, including CD29, CD34, CD44, CD45, CD73, CD90, HLA-ABC and HLA-DR (BD, PharMingen). Thereafter, the cells were analyzed by using Becton Dickinson flow cytometer (Becton Dickinson, San Jose, Calif., USA).

Figure 2:
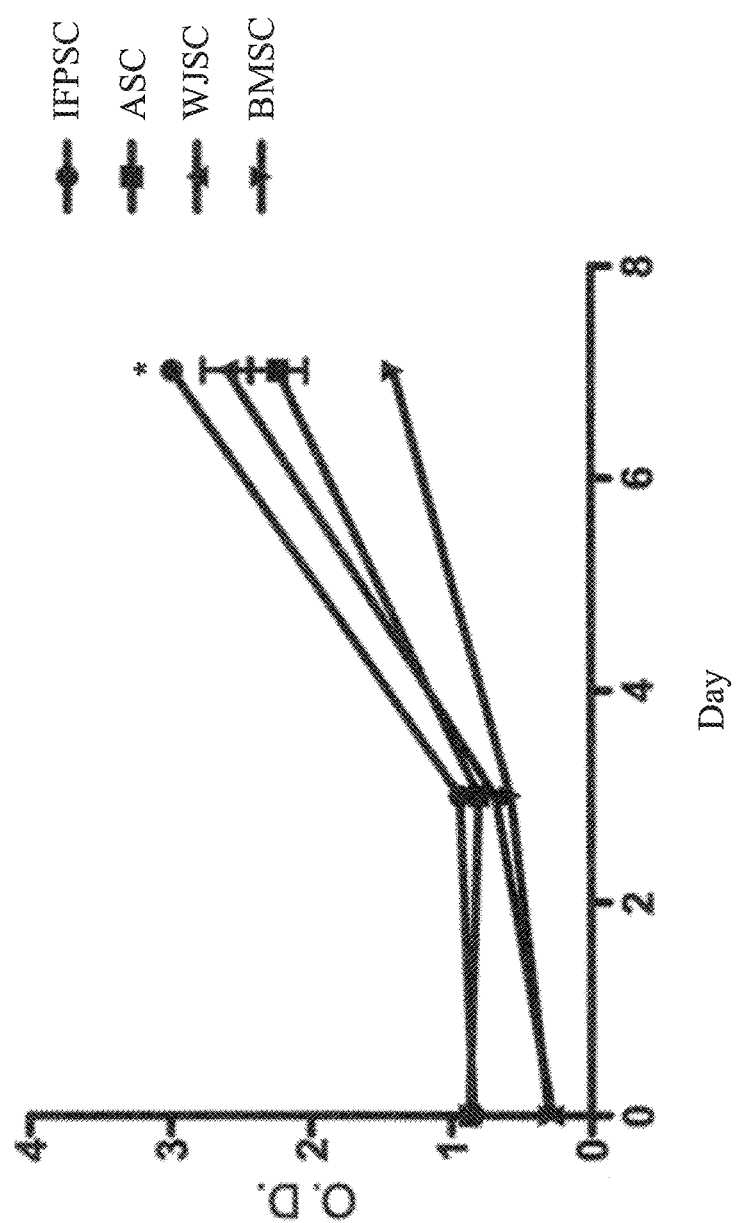
FIG. 2 shows growth kinetics of IFPSCs, BMSCs, WJSCs and ASCs from abdominal subcutaneous fat.

The results of Examples 1 to 3 show that the IFPSCs have a phenotype similar to adipose-derived stem cells. As shown in FIGS. 1A-1D, when the cells were cultured to passage 3, the derived IFPSCs has a fibroblast-like appearance with high degree of homogeneity and readily reached the confluence in days 14 of culture. Like other MSCs, the IFPSCs expresses surface markers of CD29, CD44, CD73, CD90, and HLA-ABC. However, as shown in FIGS. 1A-1D, unlike BMSCs, the IFPSCs express higher levels of CD34 and CD45. As shown in FIGS. 1A-1D and Table 1, compared to the BMSCs, WJSCs and ASCs, the IFPSCs have cell surface markers that are similar to ASCs and unlike BMSCs. As shown in FIG. 2, the cell numbers of the IFPSCs, BMSCs, WJSCs and ASCs are observed on days 0, 3 and 7. The growth kinetics of the IFPSCs are significantly better than that of the ASCs, BMSCs and WJSCs on culture day 7 ($p<0.05$).

TABLE 1

Comparison of the percentage of CD markers in different kinds of stem cells

| CD marker | IFPSCs | ASCs | WJSCs | BMSCs |
| --- | --- | --- | --- | --- |
| CD44 | 99.3% | 99.2% | 99.5% | 99.1% |
| CD90 | 95.1% | 97.0% | 98.0% | 99.9% |
| CD105 | 98.0% | 99.0% | 97.0% | 98.4% |
| CD34 | 9.0% | 11.9% | 0.2% | 0.3% |
| CD45 | 11.0% | 0.4% | 0.4% | 0.5% |
| CD56 | 1.0% | 0.4% | 0.5% | 10.0% |

Abbreviations:
IFPSCs, infra-patellar fat pad stromal cells;
ASCs, adipose-derived stem cells from abdominal subcutaneous fat;
WJSCs, Wharton jelly stem cells;
BMSCs, bone marrow mesenchymal stem cells.

Example 4 Chemotaxis Migration Assay

The cartilage fragments were minced into 1 mm$^3$ pieces and digested with type II collagenase (0.1%, Worthington, Lakewood, N.J., USA) solution overnight at 37° C. The digested contents were then filtered through a 100 μm filter and washed with PBS. The isolated chondrocytes were then seeded at 5,000 cells/cm$^2$ and grown to confluence in DMEM/F12 (Gibco) containing 2 mM L-glutamine, 10% FBS (Gibco), 1× penicillin/streptomycin, 50 μg/ml ascorbic acid, and 0.1 M non-essential amino acids (Gibco, Invitrogen, Grand Island, N.Y., USA). The chondrocyte conditioned medium was collected for 48 hours by further incubating chondrocytes in high glucose DMEM (Gibco) supplemented with 10% FBS and 1% penicillin/streptomycin.

The IFPSCs, BMSCs, ASCs, and WJSCs were seeded in the upper well of a 24-well transwell Boyden chamber (8 μm pore size; Costar, Corning Inc., Corning, N.Y., USA) and allowed to migrate towards cell-free medium derived from chondrocytes placed in the bottom wells. The migrated cells were assessed after 48 hours since migration by staining with crystal violet (Sigma-Aldrich, St Louis, Mo., USA) and counting through the bright field microscopy.

Figure 3:
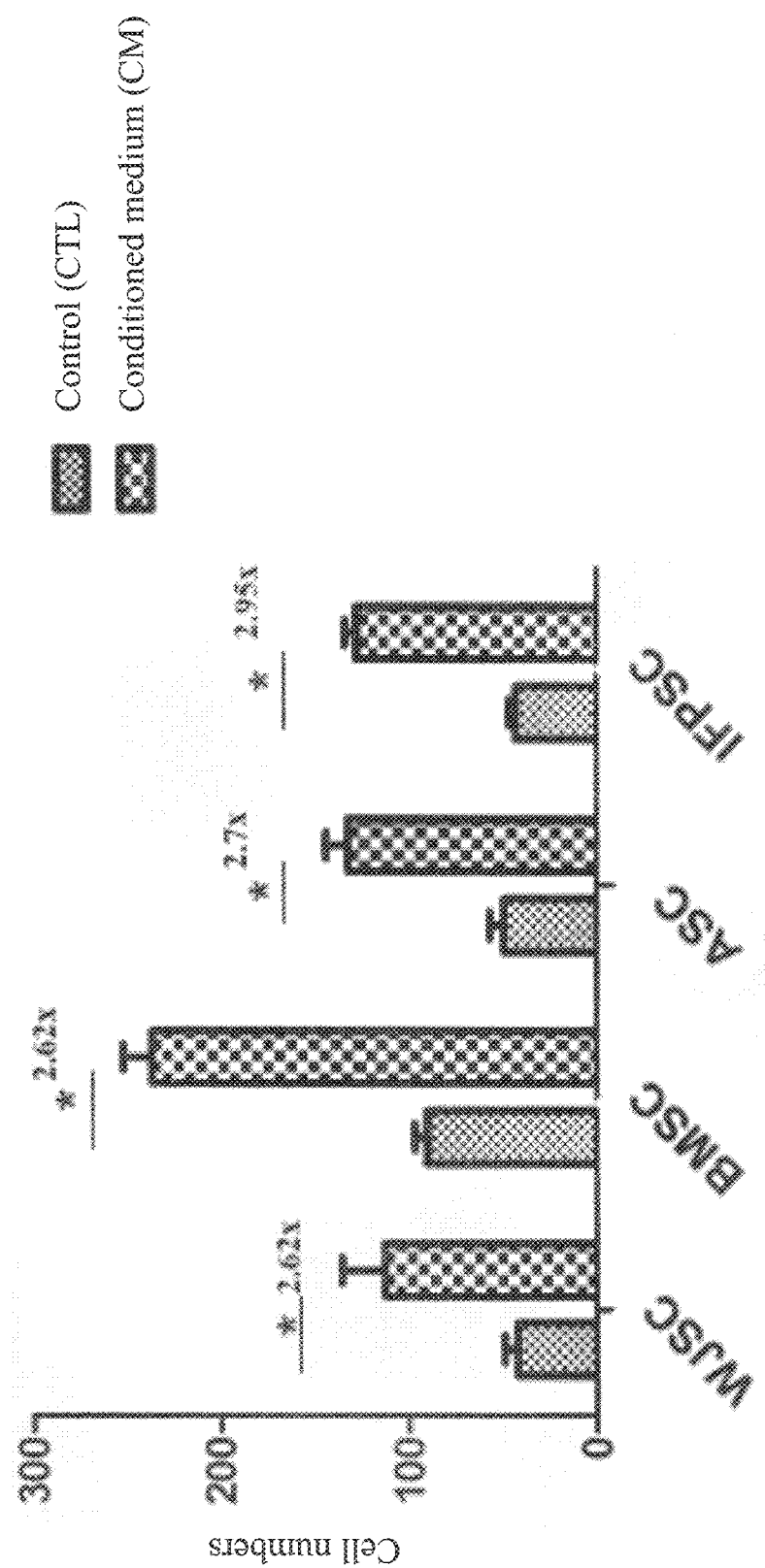
FIG. 3 shows that the mesenchymal stem cells from different origins are chemotactic to the conditioned medium (hereinafter also referred to as CM) of chondrocytes.

The results of Example 4 show that the IFPSCs are chemotactic to chondrocytes. As shown in FIG. 3, the basic migration activity of the IFPSCs in the control medium was similar to the ASCs and WJSCs but less than that of the BMSCs. All of the cells, including the IFPSCs, are highly chemotactic to the chondrocytes conditioned medium. Nonetheless, the IFPSCs have a migration ratio 2.95-fold higher than that of the control medium.

Example 5 Inductions of Adipogenesis, Osteogenesis and Chondrogenesis

The IFPSCs were seeded in a 12-well plate at a density of 5×10$^4$ cells per well with adipogenic medium (DMEM supplemented with 10% FBS, 1 μmol/L dexamethasone (Sigma-Aldrich, St Louis, Mo., USA), 5 μg/mL insulin (Sigma-Aldrich, St Louis, Mo., USA), 0.5 mmol/L isobutylmethylxanthine (Sigma-Aldrich, St Louis, Mo., USA), and 60 μmol/L indomethacin (Sigma-Aldrich, St Louis, Mo., USA). The IFPSCs were then allowed to grow for 7 days, with the medium being changed every 3 days, and then stained with Oil Red (Sigma-Aldrich, St Louis, Mo., USA). After washing twice with PBS, lipids in the sample were extracted with 1 ml 100% isopropanol (Sigma-Aldrich, St Louis, Mo., USA) and shaken gently for 5 minutes. The concentration of the lipids was measured based on the absorbance at 510 nm. The content of lipids in each sample was measured in triplicate.

The IFPSCs were seeded in a 12-well plate at a density of 1×10$^4$ cells per well and grown with osteogenic medium (DMEM supplemented with 10% FBS, 0.1 μmol/L dexamethasone, 10 mmol/L β-glycerol phosphate (Sigma-Aldrich, St Louis, Mo., USA), and 50 μmol/L ascorbic acid (Sigma-Aldrich, St Louis, Mo., USA)) and changed the medium every three days. The cells were allowed to grow for 21 days and were then stained with Alizarin Red (Sigma-Aldrich, St Louis, Mo., USA). For quantification of the staining, 800 μL 10% (v/v) acetic acid (Baker, Phillipsburg, N.J., USA) was added to each well, and the plate was incubated at room temperature for 30 minutes with shaking. The monolayer, loosely attached to the plate, was then scraped from the plate with a cell scraper (Corning Inc., Corning, N.Y., USA) and transferred with 10% (v/v) acetic acid to a 1.5 mL microcentrifuge tube with a wide-mouth pipette.

After vortexing for 30 seconds, the slurry was overlaid with 500 μL mineral oil (Sigma-Aldrich, St Louis, Mo., USA), heated exactly to 85° C. for 10 minutes, and then transferred to ice for 5 minutes. The slurry was then centrifuged at 20,000 g for 15 minutes, and then 500 μL of the supernatant was transferred to a new 1.5 mL micro-centrifuge tube (Scientific Specialties Inc., Lodi, Calif., USA). Then, 200 μL of 10% (v/v) ammonium hydroxide (Baker, Phillipsburg, N.J., USA) was added to neutralize the acid. The supernatant of each sample (150 μL) was read in triplicate at 405 nm in a 96-well plate (Costar, Corning Inc., Corning, N.Y., USA) with opaque wall and transparent bottom (Costar, Corning Inc., Corning, N.Y., USA).

The IFPSCs, ASCs, BMSCs, and WJSCs were seeded in a 12-well plate at a density of 1×10$^5$ cells/cm$^2$ and grown in the chondrogenic medium comprising DMEM, 10% FBS, 10 ng/ml TGF-β1 (Pepro Tech Inc., Rocky Hill, N.J., USA), 50 μg/ml ascorbic acid-2-phosphate (Sigma-Aldrich, St Louis, Mo., USA), and 6.25 μg/ml of insulin (Sigma-Aldrich, St Louis, Mo., USA). The medium was changed every three days. The cells were incubated with the chondrogenic medium at 37° C. with 5% $CO_2$ for three weeks. After fixing in para-formaldehyde (Bionovas, Toronto, Canada), the cells were fixed on slides and stained by using standard Alcian Blue (Fluka, Sigma-Aldrich Chemie GmbH, Buchs, Switzerland) protocols. For quantification of the incorporation level of Alcian Blue into the proteoglycan-rich extracellular matrix, the cultures were incubated with 6 M guanidine hydrochloride (Sigma-Aldrich, St Louis, Mo., USA) overnight and subjected to photometric measurement at optical density of 595 nm.

The results of Example 5 show that the IFPSCs can differentiate into fat, bone and cartilage. For the induction of differentiation in medium, the IFPSCs readily differentiate into fat, bone, or cartilage lineages. As shown in FIGS. 4A and 4B, by inducing for 14 days in adipogenic and osteogenic conditions, the isolated IFPSCs show large, oil red O-positive lipid droplets within the cytoplasm, and become positive for alizarin red staining with a change of cell morphology to cuboid shape. As shown in FIGS. 4C and 4D, by chondrogenic induction for 21 days, the IFPSCs show cell aggregation stained by Alcian Blue.

Example 6 RNA Extraction and Quantitation

The total RNA was extracted using RNeasy® (Qiagen) according to the manufacturer's instructions. The real time PCR analysis of SOX9 and COL2A1 genes (primers and annealing temperatures listed in Table 2) was performed. The complementary DNA was synthesized by using SuperScript III One-Step RT-PCR kit (Invitrogen, Grand Island, N.Y., USA) and amplified by AmpliTaq Gold Kit (Applied Biosystems, Foster City, Calif., USA). Real-time PCRs were performed and monitored by using FastStart universal SYBR green master (ROX, Roche, Indianapolis, Ind., USA) and quantitative real-time PCR detection system (ABI Step One Plus system, Applied Biosystems, Foster City, Calif., USA). The gene products were analyzed with the GAPDH gene as a reference. The expression level of each target gene was then calculated as $2^{\Delta\Delta C_t}$. Four readings of each experimental sample were performed for each gene of interest and the experiments were repeated at least three times.

TABLE 2

Sequences of primers and conditions used in real-time polymerase chain reaction

| Gene | Forward sequence | Reverse sequence | Annealing temperature (° C.) |
|---|---|---|---|
| SOX9 | 5'-CTT CCG CGA CGT GGA CAT-3' (SEQ ID NO: 1) | 5'-GTT GGG CGG CAG GTA CTG-3' (SEQ ID NO: 2) | 55 |
| COL2A1 | 5'-CAA CAC TGC CAA CGT CCA GAT-3' (SEQ ID NO: 3) | 5'-TCT TGC AGT GGT AGG TGA TGT TCT-3' (SEQ ID NO: 4) | 60 |
| GAPDH | 5'-TCT CCT CTG ACT TCA ACA GCG AC-3' (SEQ ID NO: 5) | 5'-CCC TGT TGC TGT AGC CAA ATT C-3' (SEQ ID NO: 6) | 60 |

The results of Example 6 show that the IFPSCs were more chondrogenic than the mesenchymal stem cells (such as BMSCs, ASCs and WJSCs) derived from other sites. As shown in FIGS. 5A and 5B, For the induction of chondrogenic differentiation, on day 21, the induced IFPSCs express much larger amounts of glycosaminoglycan (Alcian Blue) than the induced BMSCs, ASCs, and WJSCs. As shown in FIGS. 5C and 5D, the IFPSCs progressively express chondrogenic genes such as SOX9 and COL2A1. On the contrary, these two genes are either less-expressed in ASCs and WJSCs or inconsistently-expressed at different induction durations in BMSCs.

Example 7 Cell Culture in HA Micro-Environment

Different amounts of hyaluronan solutions (molecular weight 5000 to 10000 KDa, 20 mg/2 ml, Suplasyn, BIONICHE, Galway, Ireland) dissolved in culture media were added into a 12-well plate for achieving final concentrations (v/v) being 25%, 50%, 75%, and 100%, and allowed to solidify in room air. The IFPSCs were seeded at a density of 5000 cells in 100 μl KSFM containing 5% FBS, NAC, and L-ascorbic acid 2-phosphate. The medium was changed every 2 days over 14 days. The cells were collected for further differentiation and proliferation analysis at different time points.

Figure 6A:
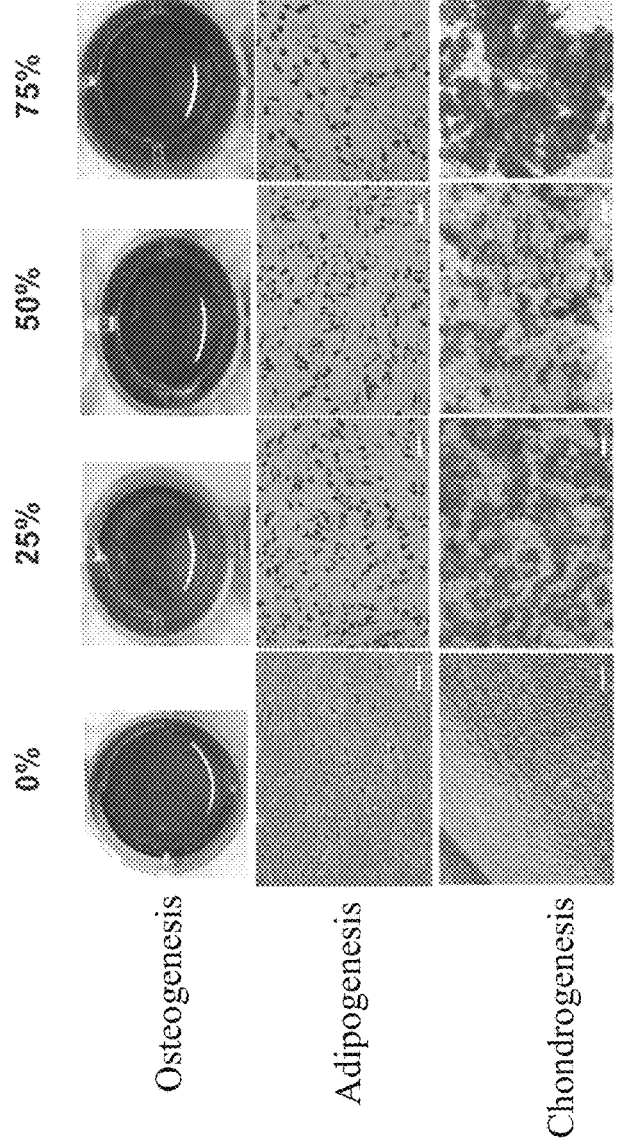
FIGS. 6A and 6B show that 25% (v/v) hyaluronan enhances adipogenesis, osteogenesis, and chondrogenesis of the IFPSCs. Gross pictures (FIG. 6A) and staining level (FIG. 6B) of osteogenesis, adipogenesis, and chondrogenesis of the IFPSCs cultured at different concentrations of HA are shown as indicated by Alizarin red, Oil red, and Alcian blue staining, respectively: $*p<0.05$, $p<0.01$, $*p<0.001$.
Figure 6B:
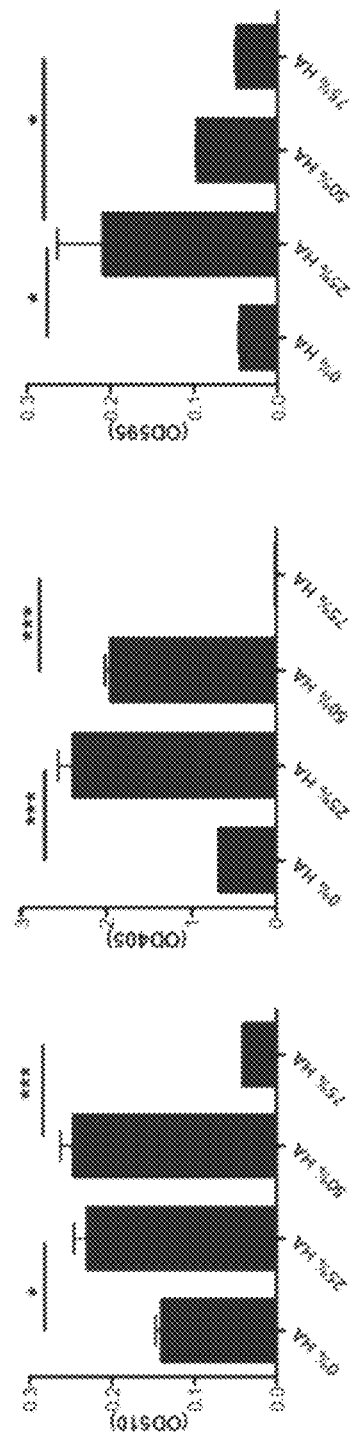
Figure 7A:
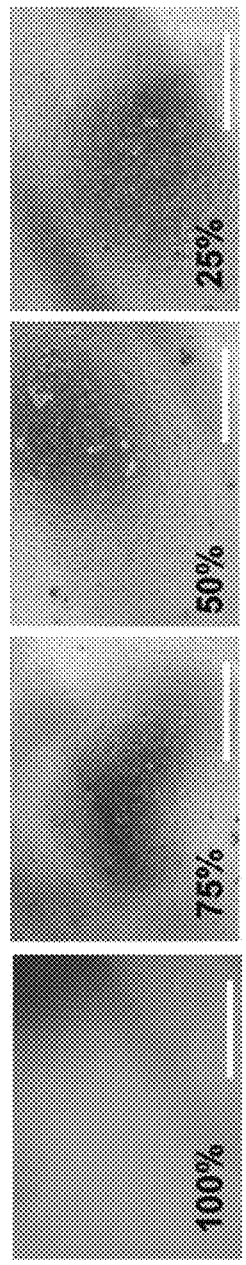
FIGS. 7A and 7B show that hyaluronan (HA) has no effect on the IFPSCs proliferation.
Figure 7B:
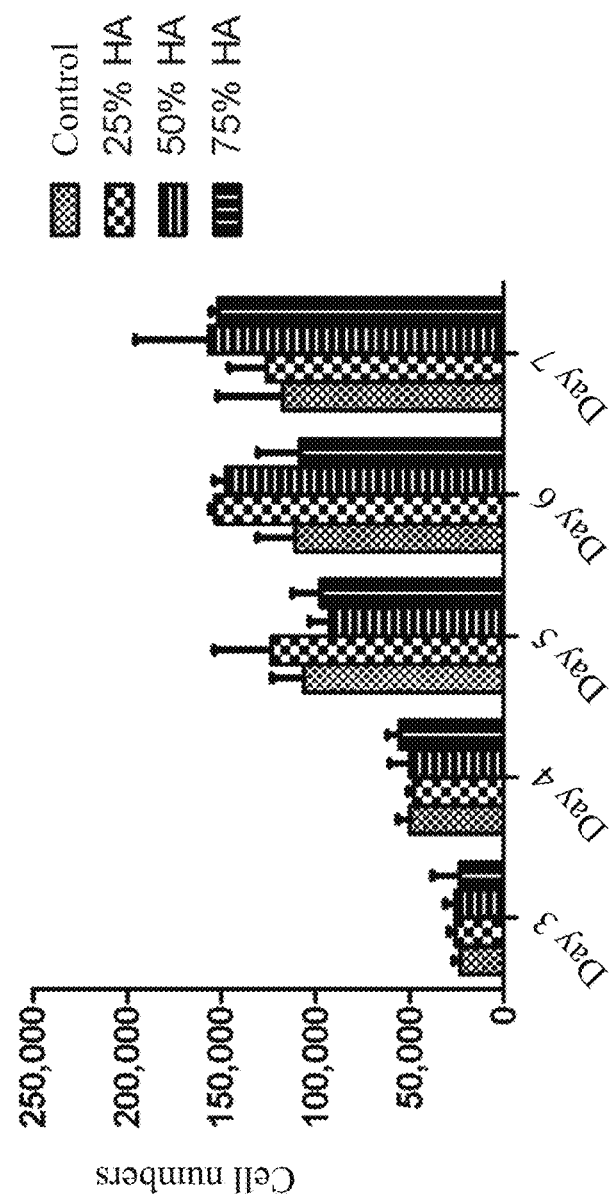

The results of Example 7 show that the HA microenvironment enhances the differentiation of IFPSCs but was neutral to its growth. At different concentrations, HA was coated on the culture dishes and tested for the effect on the differentiation and growths of IFPSCs. Other than the 75% (v/v) HA-coated culture, which shows a poor differentiation capability, the IFPSCs cultured with either 25% (v/v) or 50% (v/v) HA have enhanced osteogenic, adipogenic, and chondrogenic differentiations. As shown in FIGS. 6A and 6B, for chondrogenesis, the IFPSCs cultured with 25% (v/v) HA show the best capacity for differentiation, with 2- to 3-fold increases compared to the culture without HA (p<0.01). Moreover, as shown in FIGS. 7A and 7B, the cultures coated with HA in the concentrations varying from 25% (v/v) to 75% (v/v) do not affect the proliferations of the IFPSCs.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claim.

What is claimed is:

1. A pharmaceutical composition comprising mesenchymal stem cells, a hyaluronan and a pharmaceutically acceptable carrier, wherein the mesenchymal stem cells are cultured to passage 3 to passage 6 and are infra-patellar fat pad stromal cells, and the hyaluronan has a molecular weight of between 5000 to 10000 KDa and a concentration in a range from 2.5 mg/ml to 5.0 mg/ml.

2. The composition of claim 1, which is useful for treating a joint disease.

3. The composition of claim 2, wherein the joint disease is articular cartilage defect, chronic articular rheumatism, arthritis deformans or periarthritis humeroscapularis.

4. The composition of claim 1, comprising $1.6 \times 10^7$ to $1 \times 10^9$ cells of the mesenchymal stem cells.

5. The composition of claim 1, wherein the concentration of the hyaluronan is 2.5 mg/ml.

6. A method for treating a joint disease comprising: administrating an effective amount of the composition of claim 1 to an injured joint tissue of a subject.

7. The method of claim 6, wherein the mesenchymal stem cells are induced to produce glycosaminoglycans.

8. The method of claim 6, wherein administrating is by injection.

9. The method of claim 6, wherein the joint disease is articular cartilage defect, chronic articular rheumatism, arthritis deformans or periarthritis humeroscapularis.

10. The method of claim 6, wherein the composition comprises $1.6 \times 10^7$ to $1 \times 10^9$ cells of the mesenchymal stem cells.

* * * * *